United States Patent [19]

Church

[11] Patent Number: 4,942,124
[45] Date of Patent: Jul. 17, 1990

[54] MULTIPLEX SEQUENCING

[75] Inventor: George M. Church, Boston Mass.

[73] Assignee: President and Fellows of Harvard College, Cambridge, Mass.

[21] Appl. No.: 228,596

[22] Filed: Aug. 4, 1988

Related U.S. Application Data

[63] Continuation-in-part of Ser. No. 084,623, Aug. 11, 1987.

[51] Int. Cl.⁵ ............................................. C12Q 1/68
[52] U.S. Cl. .................................... 435/6; 435/172.3; 435/803; 436/501; 935/23; 935/24; 935/29; 935/77; 953/78
[58] Field of Search ................ 435/6, 803, 172.3, 320; 536/27; 436/501; 935/77, 78, 23, 24, 29

[56] References Cited

U.S. PATENT DOCUMENTS

| | | |
|---|---|---|
| 4,302,204 | 11/1981 | Wahl et al. . |
| 4,359,535 | 11/1982 | Pieczenik ............................ 435/317 |
| 4,528,266 | 7/1985 | Pieczenik ................................ 435/6 |
| 4,588,682 | 5/1986 | Groet et al. ............................. 435/6 |
| 4,594,318 | 6/1986 | Gusella et al. .......................... 435/6 |
| 4,713,326 | 12/1987 | Dattagupta et al. .................... 435/6 |
| 4,729,947 | 3/1988 | Middendorf et al. ................... 435/6 |
| 4,752,566 | 6/1988 | Collins et al. ........................... 435/6 |

FOREIGN PATENT DOCUMENTS 224126  6/1987  European Pat. Off. .

OTHER PUBLICATIONS

Church et al., "Genomic Sequencing", *Proc. Natl. Acad. Sci.*, vol. 81, pp. 1991–1995, Apr. 1984.

Roger Lewin, "National Academy Looks at Human Genome Project, Sees Progress", *Science*, vol. 235, pp. 747–748, Feb. 1987.

Larry Thompson, "Genes, Politics and Money", *Washington Post Health*, Feb. 24, 1987.

Department of Energy, Office of Health and Environmental Research, "Sequencing the Human Genome", Summary Report of the Santa Fe Workshop, 3/3–4 (1986).

Compton et al., "The TurboBlot TM Processing System: Improved Southern/Dot Blot Handling and Analysis", *BioTechniques*, vol. 3, No. 4, pp. 308–312 (1985).

Delehanty et al., "Approaches to Determining Mutation Rates in Human DNA", *Mutation Research*, 167 (1986), pp. 215–232.

Church et al., *Science*, 240:185, 1988, "Multiplex DNA Sequencing".

Elder et al., "Automatic Reading of DNA Sequencing Gel Autoradiographs Using a Large Formal Digital Scanner", *Nucleic Acids Research*, 14:417, 1986.

Weiss et al., "Multiplexed Dideoxy DNA Sequencing", Abstracts of Papers Presented at the 1988 Meeting on Genome Mapping and Sequencing, 4/27–5/1, 1988.

(List continued on next page.)

*Primary Examiner*—Amelia Burgess Yarbrough
*Attorney, Agent, or Firm*—Fish & Richardson

[57] ABSTRACT

This invention features vectors and a method for sequencing DNA. The method includes the steps of:

(a) ligating the DNA into a vector comprising a tag sequence, the tag sequence includes at least 15 bases, wherein the tag sequence will not hybridize to the DNA under stringent hybridization conditions and is unique in the vector, to form a hybrid vector, (b) treating the hybrid vector in a plurality of vessels to produce fragments comprising the tag sequence, wherein the fragments differ in length and terminate at a fixed known base or bases, wherein the fixed known base or bases differs in each vessel, (c) separating the fragments from each vessel according to their size, (d) hybridizing the fragments with an oligonucleotide able to hybridize specifically with the tag sequence, and (e) detecting the pattern of hybridization of the tag sequence, wherein the pattern reflects the nucleotide sequence of the DNA.

12 Claims, 7 Drawing Sheets

OTHER PUBLICATIONS

Sanger et al., "Cloning in Single-Stranded Bacteriophage as an Aid to Rapid DNA Sequencing", *J. Mol. Biol.*, No. 143, pp. 161–178 (1980).

Wallace, et al., *Nucleic Acids Research,* vol. 9, No. 4, pp. 879–894 (1981).

Korneluk et al., *Biological Abstracts,* vol. 81, Abstract No. 81111384 (1985).

*Gene,* vol. 40, No. 2/3, pp. 317–324 (1985), Korneluk et al.

Singer-Sam, J. et al., Proc. Natl. Acad. Sci. USA 80:802–806 (1983).

Kalyan, N. K. et al., Gene 42:331–337 (1986).

Estivill et al., Nucleic Acids Research 15:1415–1425 (1987).

Rougeon, F. et al., Gene 1:229–239 (1977).

Lin, Y., In Genetic Engineering Techniques: Recent Developments Academic Press, NY, 1982, pp. 111–127.

FIG. 2

```
                                                              T C
                                                              T G
                                                              C-G
                                                              G-C
                                                              C-G
                                                              C-G
                                                              C-G
                                                              A-T
                                                              A-T
                                                              A-T
                                                              A-T
     T C
     G T
     C-G
     G-C
     T-A
     C-G
     G-C
     C-G
     C-G
ATTAAAAAA  CCGC-H26-GGTACCC-!-GGGAGCTC-D25-GCGGCCGCGAATTC  TT CTG
  ter      Pst Not         Kpn Sma Sac            Not      Eco rpoC-ter
```

FIG. 3

```
01 P   CCTTTCATTACAACTAATCA TAACAT.
02 P   CATAAATTATTCTACTTATA AAAAATA
03 P   CAACTCCTATCAACTCTACA CTTACTC
04 P   CAATATTTAAACCTCACACT TCCAATA
05 P   CATAATATAACCTAAACCCT AAATCTT
06 P   CCACATCCAAAATAATCAAT CAACATA
07 P   CTACTAAATTTCCTTTATAA TCCCCAA
08 P   CCCCTCCAATATAATATATA ATTACAT
09 P   CATTAACAATCATACCACTA CCAAATA
10 P   CCTAATCATCAATATACTCA ATACAAC
11 P   CATCACCACACATATTATCC TTATCCT
12 P   CTAATCTATTAACCACTTAA AATACTT
13 P   CAACTTACTCTACACCCCTT TTATCAC
14 P   CTCTTCATAATATAATTTAC TACTCTT
15 P   CAAACCAACATTTAACACAA TATATCA
16 P   CATAAACACCCATTCATCCA ACTCTTA
17 P   CTCACCTTCTTAAAACCCAA ATTCTCT
18 P   CAAATCTACTTCCAACCACT ATTCAAA
19 P   CAACCAACTCTACTTATCAC TCCCAAC
20 P   CCCCACCAAATTACAACTAC AATACTC
00 P   CCTTCCTAAACCACACTCCA TTTAACC

01 E   CCCCCAATAAAATCATACTA CCTTAT
02 E   CTTTTACACAATAACTCTTA CTCAAA
03 E   CTAACAACAAACCTTACTAC ATCCTA
04 E   CAACACCCATCCACTAAACT TAAACA
05 E   CACATAACTCAAATCTCAAA TTCACC
06 E   CACCCCATATCAATTTACAA TAATCT
07 E   CCATAAACTCCTCATCTTCC CCACTC
08 E   CCTCTTCCCATTTTTATTAT TACTTC
09 E   CTATTCACAATACACCACCA CAATCC
10 E   CACCTAATACCCTATATATA ATACCA
11 E   CCACCTTTATACTTCTTACA ACTCAT
12 E   CCCTTCTACCAACCTATATC ATTTAT
13 E   CAAAAACTAATTCCCAAAAA ATCCTC
14 E   CTTTCTTTTCTCAACCCCTT CACCCA
15 E   CTCACTAAATCTTATCTTAC TTTACA
16 E   CTTACAATCCCTATCATAA CATTAT
17 E   CCACCATCTTCACCCCCCAA TTTAAT
18 E   CAACCACAACCAACCCTACT CCCCTA
19 E   CCAACCCTACATTAACTTCT ATCATC
20 E   CCATAACTTTAACCTTTAAC ATTAAT
00 E   CTTCCTCTTTATCTTTATTA ACATTT
```

MULTIPLEX SEQUENCING

This invention was made with support from the U.S. Government, specifically DOE Grant DE-FG02-87ER60565; the U.S. Government has rights in the invention.

BACKGROUND OF THE INVENTION

This application is a continuation-in-part of Church, U.S. Ser. No. 084,623, filed Aug. 11, 1987, entitled MULTIPLEX SEQUENCING, assigned to the same assignee as the present application and hereby incorporated by reference herein.

This invention relates to sequencing of DNA.

The sequence of nucleotide bases in DNA is generally determined using the methods described by Maxam and Gilbert (65 Methods Enzymol. 497, 1980) or by Sanger et al. (74 *Proc. Natl. Acad. Sci. USA* 5463, 1977). These methods generally involve the isolation of purified fragments of DNA prior to sequence determination.

Church et al. (81 *Proc. Natl. Acad. Sci.* 1991, 1984) describe a method of sequencing directly from genomic DNA. Unlabelled DNA fragments are separated in a denaturing gel after complete restriction endonuclease digestion and partial chemical cleavage of the genome. After binding these fragments to a nylon membrane the DNA is hybridized with a probe comprising RNA homologous to the region near to the region to be sequenced. The membrane can be reprobed with other probes to sequence other regions of interest.

SUMMARY OF THE INVENTION

In a first aspect, the invention features a set comprising at least two vectors. Each vector of the set has a DNA construct having at least one restriction endonuclease site. Further, each vector of the set differs from each other vector of the set only at a tag sequence. The tag sequence includes at least 15 base pairs and is located within 50 bases of a restriction endonuclease site. Further, each tag sequence in the set will not hybridize under stringent hybridization conditions to another tag sequence in the set. By stringent hybridization conditions is meant low enough salt counterion concentration and high enough temperature to melt mismatched duplexes, to form single stranded molecules (e.g., at 42° C. in 500–1000 mM sodium phosphate buffers). By vector is meant any fragment of DNA, whether linear or circular, which can be ligated to DNA to be sequenced. Such vectors may include an origin of DNA replication.

In a related aspect the invention features a vector for sequencing DNA. The vector comprises a DNA construct having two restriction endonuclease sites, each site being recognised by a first restriction endonuclease, wherein treatment of the vector with this first endonuclease produces a discrete DNA fragment consisting of the DNA extending between the sites. The vector further includes two tag sequences both being located on the DNA fragment, and separated from each other by a second restriction endonuclease site. The tag sequences include at least 15 base pairs and both ends of the tag sequences are located within 50 bases of the nearest first restriction site and within 50 bases of the second restriction endonuclease site. The tag sequences are unique in the vector. By unique is meant that there are no other nucleotide sequences in the vector which exactly correspond to the tag sequences.

In preferred embodiments of these aspects the tag sequences have two strands, one of which is free from cytosine residues; the vectors are produced from a parental vector having randomly formed tag sequences ligated into it; and the randomly formed sequences are formed in a DNA synthesizer supplied with at least two nucleotides at each addition step.

In another related aspect, the invention features a set of tag oligonucleotides which bind to the tags in the vector, wherein each tag oligonucleotide of the set is unique in the set and neither tag oligonucleotide nor an oligonucleotide homologous to the tag oligonucleotide will hybridize under stringent hybridization conditions to DNA in the set. Each such oligonucleotide is at least 15 bases in length.

In preferred embodiments the set of vectors described above is produced by ligation into a parental vector of this set of tag oligonucleotides.

In a second aspect, the invention features a method for sequencing a DNA specimen, termed multiplex sequencing. The method includes the steps of:

(a) ligating the DNA specimen into a vector comprising a tag sequence, to form a hybrid vector. The tag sequence includes at least 15 bases, will not hybridize to the DNA specimen under stringent conditions, and is unique in the vector;

(b) treating separate aliquots of the hybrid vector in a plurality of vessels to produce fragments each comprising the tag sequence. These fragments in each vessel differ in length from each other and all terminate at a fixed known base or bases (e.g., A, T, C or G for Sanger dideoxy sequencing; G, A+G, T+C, T or C for Maxam and Gilbert sequencing). The fixed known base or bases differ from these in other vessels;

(c) separating the fragments from each vessel according to their size;

(d) hybridizing the fragments with an oligonucleotide able to hybridize specifically with the tag sequence; and (e) detecting the pattern of hybridization of the oligonucleotide; this pattern reflects the nucleotide sequence of the DNA specimen.

In preferred embodiments, the method further includes the step of ligating the DNA specimen to a plurality of vectors to form a plurality of hybrid vectors; each vector differs from each of the others at a tag sequence and each tag sequence is unable to hybridize under stringent conditions to other tag sequences; the method further includes the step of rehybridizing the fragments with each oligonucleotide corresponding to each tag sequence of each vector; each vector includes two tag sequences; the method further comprises binding the fragments to a solid support prior to the hybridizing step; the method further includes, prior to the separating step, providing a molecular weight marker in one vessel and detecting this marker after the separating step; and the solid support comprises the vector or the oligonucleotide, wherein the vector or oligonucleotide acts as an identifying marker for the support.

In a third aspect, the invention features a method for repeatedly hybridizing a solid support, comprising nucleic acid, with a plurality of labels, including the steps of:

(a) enclosing the support within a container comprising material thin enough to allow detection of hybridization of nucleic acid with the labels, (b) inserting hybridization fluid comprising a first label into the container, (c) removing the hybridization fluid from the container, and (d) detecting hybridization of the first label to the solid support, while the solid support remains in the container.

In preferred embodiments the method further comprises, after the detecting step, repeating steps b, c and d using a second label; and most preferably comprises repeating steps b, c and d at least 20 times with at least 20 labels.

In a fourth aspect, the invention features a method for determining the DNA sequence of a DNA specimen, including the steps of:

(a) performing a first sequencing reaction on the DNA specimen;

(b) performing a second sequencing reaction on a known DNA specimen;

(c) placing corresponding products of the first and second sequencing reactions in the same lanes of a DNA sequencing gel;

(d) running the products into the gel;

(e) detecting the location of the products in the gel, and (f) using the location of the known DNA products to aid calculation of the DNA sequence of the DNA specimen.

In a fifth aspect, the invention features an automated hybridization device, for repeatedly hybridizing a solid support containing nucleic acid, with a plurality of labels. The device includes a container enveloping the solid support, formed of material thin enough to allow detection of hybridization of the nucleic acid with a label by placement of a label-sensitive film adjacent the container. Also included is an inlet and outlet for introducing and withdrawing hybridization fluid and means for automatically regulating introduction and removal of hybridization fluid.

In preferred embodiments the automated hybridization device includes inflatable means for contacting the container with the film; a lightproof box enveloping the container; and a plurality of containers, each separated by a label-opaque shelf.

Multiplex sequencing significantly increases the speed at which DNA sequencing can be performed. Specifically, it reduces the experimental time for preparation of the DNA for sequencing, for the base specific chemical reactions (when using the Maxam and Gilbert methodology) and for the Sanger dideoxy reactions, for the pouring and running of sequencing gels, and for reading the image and sequence data from autoradiographs of these gels.

The above vectors are specifically designed for multiplex sequencing having unique DNA sequences positioned appropriately such that each sequence provides a specific probe region for DNA inserted into the vector, and indeed for each strand of the inserted DNA. Thus, any DNA inserted into these vectors is readily sequenced, as a pool of such inserts.

Other features and advantages of the invention will be apparent from the following description of the preferred embodiments and from the claims.

DESCRIPTION OF THE PREFERRED EMBODIMENTS

The drawings will first briefly be described.

Drawings

FIG. 2 is the nucleotide sequence of part of a multiplex vector, including the tag sequences.

FIG. 3 is the nucleotide sequences of a set of tag sequences lacking G residues.

Multiplex Vectors

Multiplex vectors are used to form a set of vectors suitable for multiplex sequencing. The vectors are provided with a DNA sequence having (a) a cloning site, (b) at least one tag sequence and (c) optional removal sites. The cloning site is a position at which the DNA specimen to be sequenced is placed, usually it is a restriction endonuclease site. The vectors are provided with at least one, and preferably two, tag sequences, or probe hybridization sites. A tag sequence is an unique DNA sequence of between about 15-200 base pairs, preferably greater than 19 base pairs in length, which will act to specifically identify each vector in hybridization tests These sequences preferably have no homology elsewhere on the vector and no homology to the genomic DNA to be sequenced. Thus, positive hybridization using a part or the whole of a tag sequence as a probe for a mixture of multiplex vectors specifically identifies the multiplex vector containing this tag sequence. Further, since it is preferable that no two tag sequences are the same on a single vector, and since each strand of any one tag sequence is unique, a specific strand of the vector can also be specifically identified. Removal sites are useful when using the vectors for Maxam and Gilbert type sequencing. Generally, these sites are restriction endonuclease sites, preferably acted upon by the same restriction enzymes, and allow removal of a fragment of DNA, including the tag sequences and the DNA specimen to be sequenced.

The tag sequences are positioned close (preferably within 50 bases) to the cloning site, such that the DNA specimen to be sequenced can be placed between the two tag sequences, or at least downstream from one tag sequence. Further, the tag sequences are preferably positioned between two identical restriction endonuclease sites (removal sites) so that the cloned DNA and tag sequences can be readily isolated as a single fragment by digestion with the specific endonuclease.

Those skilled in the art will recognize that vectors having a single tag sequence may be used in this invention, or even vectors having more than two tag sequences. Such multi-tag vectors will preferably have multiple cloning sites for accepting different DNA fragments to be sequenced.

Example 1: TcEN vectors

Figure 1:
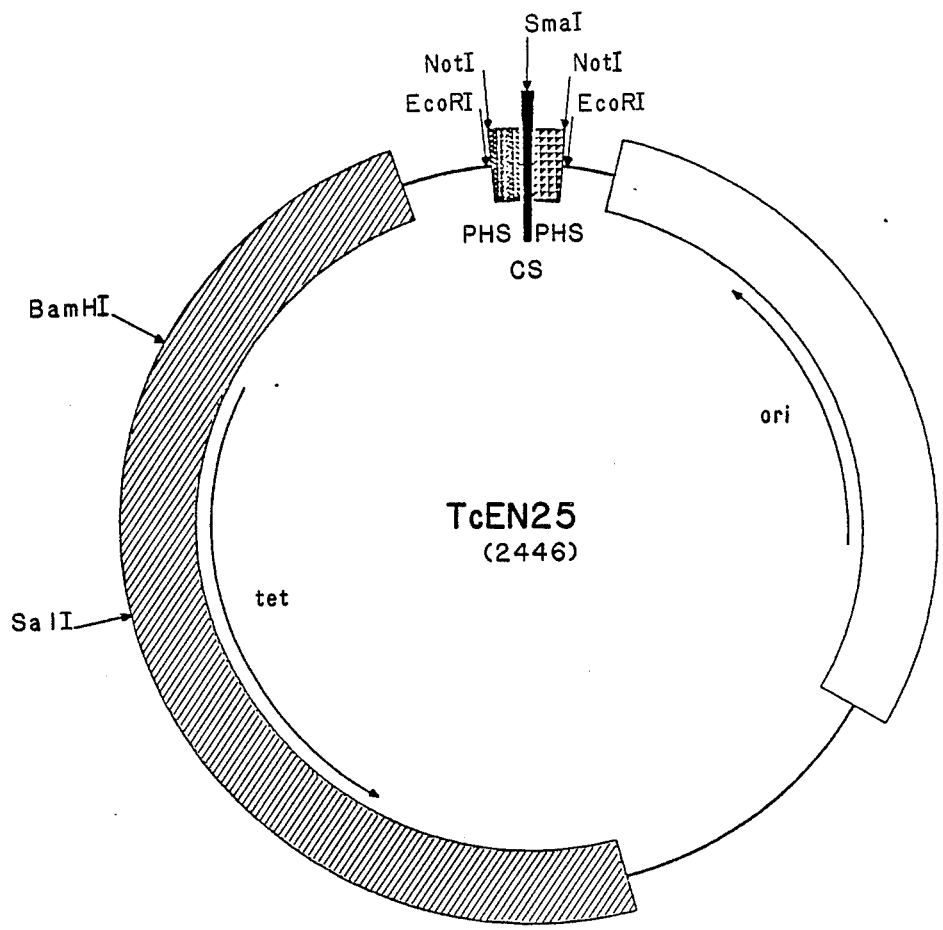
FIG. 1 is a diagrammatic representation of a multiplex vector.

An example of such a set of vectors is shown in FIG. 1. In this set of vectors, termed TcEN vectors, each vector has its own pair of unique tag sequences (labelled PHS) separated by SmaI site (the cloning site) and surrounded by NotI sites (removal sites). The unique tag sequences are generated by synthesizing oligonucleotides approximately 20 nucleotides in length in a DNA synthesizer, with all 4 nucleotides provided at each polymerization step. All $4^{20}$ possible 20-mer nucleotide sequences are produced by this procedure. The oligomer mixture was ligated into a parent TcEN plasmid to form constructs containing the sequence (NotI restriction site)—(oligomer tag sequence 1)—(SmaI site)—(oligomer tag sequence 2)—(NotI site) using standard procedures. The parent plasmid and each TcEN plasmid contain a tetracycline resistance gene which may be used for selection of clones containing these vectors. Also provided is an origin or replication (*ori*) which functions in *Esherichia coli*.

Many recombinant vectors from the original mass ligation were cloned and sequenced, and forty-six different vectors (containing 92 unique oligomer tag sequences) were chosen for initial experiments on the basis of their having the complete tag sequence-containing construct and sufficient sequence diversity to insure uniqueness. Probe oligomers (tag probes) complementary to each of the tag sequences have been prepared synthetically and radioisotopically labelled. Other labels are equally suitable; e.q., fluorescent, luminescent and enzymatic (colorimetric) labelled probes

Example 2: NoC vectors

A major problem with both dideoxy and chemical sequencing is the formation of hairpins during electrophoretic separation of the sequence reaction products. The hairpins often cause two or more base positions to comigrate on the gels causing an artifact which can be hard to notice or decipher. One partial solution, sequencing of the opposite nucleotide strand, can fail if there are tandem or alternative hairpins, or if the opposite strand has any other artifacts. Other methods, include the use of hot formamide gels, dITP, or $dc^7$GTP.

Cytosines can be chemically modified so that they will not base pair with guanines. Although cytosine chemical modification eliminates hairpins, (since at least two GC base pairs are required to stabilize a hairpin in sequencing gels containing 7M urea at 50° C.). They also prevent the GC base pair formation required for most tag probes to be able to bind to identify specific vectors later in the sequencing process. This problem is overcome by preparing a set of NoC vectors having tag sequences which completely lack cytosines on one strand (any guanines on the complementary strand) for at least 15 nucleotides in a row (FIGS. 2 & 3). These vectors generally have two such oligonucleotide tag sequences flanking each cloning site.

Referring to FIG. 2, the NoC vectors were derived from the TcEN vectors by substituting the sequence shown at the EcoRI sites. H26 represents various combinations of 26 A, C, and T nucleotides present on the strand at this point. D25 represents 25 A, G, and T's. These were chemically synthesized as a mixture (as described above in example 1) and specific examples were cloned and sequenced (see FIG. 3). The object is to have No Cytosines on the appropriate strand in the tag sequence which can be modified by chemical hairpin suppression reactions.

Referring to FIG. 3, the sequences of the tag sequence of the NoC multiplex vectors of FIG. 2 are given. The first twenty nucleotides have also been synthesized as probes. The sequences are all oriented 5' to 3', left to right The 5 terminal nucleotides shown are the 3'-most cytosines of the NotI sites. The letter P indicates that the tag sequence is closest to the PstI site; the letter E that the tag sequence is closest to the EcoRI site. The numbers are the vector and tag sequence (or tag probe) numbers; number 00 is the standard plasmid used to provide an internal control of known sequence. The NotI site adjacent to the PstI site has one C deleted so that NotI cleavage of this vector and probing with tag sequence E00 gives a 2500 base long set of sequence markers (3'end-labeled as with the unknown sequences).

These vectors also incorporate bacterial transcription terminator sequences flanking the tag sequences, to suppress excessive transcription across the boundary between foreign DNA and the vector DNA and thus promote efficient replication.

Multiplex sequencing method

Multiplex sequencing is a method for keeping a large set of DNA fragments as a precise mixture throughout most of the steps of DNA sequencing. Each mixture can be handled with the same effort as a single sample in previous methods, and so a greater total number of fragments can be handled within a fixed time period. The mixture must be deciphered at the end of the process. This is done by tagging the fragments at the beginning of the process with unique DNA sequences (tags) and then, at the end of the process, hybridizing complementary nucleic acid (probes) to the sequencing reactions which have been spread out by size, and immobilized on large membranes. Many different sequences are obtained from each pool by hybridizing with a succession of end-specific, strand-specific probes. Thus, in this procedure DNA purifications, base specific reactions and gel loadings normally done on individual fragments are replaced by operations on pools of fragments (e.q., about 46 fragments per pool). In general, the steps in the process are cloning of genomic DNA into a set of multiplex vectors, mixing one clone derived from each vector to form a pool of vectors, performing sequencing reactions on each pool of such vectors, running these reactions on a sequencing gel, binding the DNA fragments in the gel to a solid support, and probing this support with tag probes specific for each vector to identify the DNA sequence of any one cloned fragment.

This methodology can be used to sequence DNA in combination with any standard sequencing procedure, for example, nested deletions (Henikoff, 28 Gene 351, 1984), cDNA (Okayama et al. 2 Mol. Cell. Biol. 161, 1981), shotgun (Sanger et al. 162 J. Mol. Biol. 729, 1982) or DNA hybridization techniques; and can be combined with amplification methodology, for example, the polymerase chain reaction system of Saiki et al. (230 Science 1350, 1985.)

Example 3: Sequencing *Escherichia coli* genomic DNA

Figure 4:
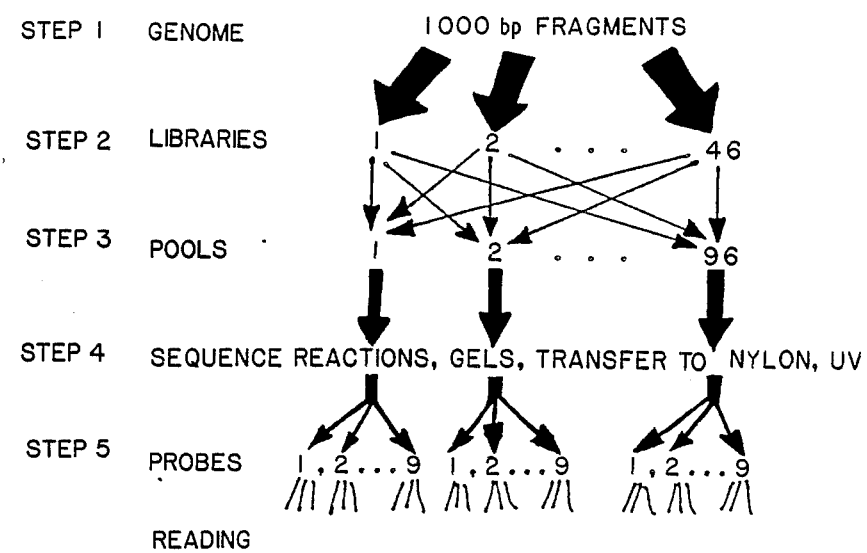
FIG. 4 is a schematic diagram representing the steps in the method of multiplex sequencing.

In this example, the steps of the multiplex sequencing process are described below, with reference to FIG. 4.

Step 1.

Genomic DNA (or equivalent large DNA fragments) of *Escherichia coli* was sonically fragmented and electrophoretically separated out for further processing. The fraction containing fragments of 800–1200 bp in length was isolated, since this size is optimal for sequencing. This treatment assures that virtually all possible DNA sequences from the original DNA are represented in a fraction of convenient molecular size for further processing.

Step 2.

The sonically fragmented and sized fraction was treated with the enzymes Bal31, and T4 polymerase, to produce blunt-ended fragments. Aliquots of the blunt ended fragment mixture were then ligated separately into each of the set of 46 TcEN multiplex vectors and cloned to produce 46 different libraries. Each library contains clones of a large representative sample from the original sonic fraction. All fragments in any library contain the tags derived from the cloning vector used to produce the library, one at each end of each strand.

Each library was then spread or "plated" onto an agar plate under limiting dilution conditions (conditions such that individual bacteria will be isolated from each other on the plate, and will form separate clonal colonies). The plates contained tetracycline so that only cells which have acquired a TcEN plasmid, with its tetracycline-resistance gene will survive. There were 46 such plates, and about 100 colonies were established per plate. After a period to allow the individual bacteria to grow into colonies, one clone (i.e., one colony, which will contain offspring of a single bacterium) from each of the 46 plates was then mixed together to form a pooled sample. This pooled sample contained a single clone, containing a single approx. 1 kb fragment, from each of the 46 libraries—that is, 46 different 1 kb fragments of the original DNA sample. Each fragment is labeled at each end with the tag oligomers unique to the library from which it was produced. 96 such pooled samples were made.

Step 4.

Each of the pooled samples was treated via the Maxam-Gilbert nucleotide sequencing procedure to produce a large number of DNA fragments of differing length. Each fragment will contain one of the tag sequences at one end. Some of these chemical sequencing reactions were performed in standard 96 well microtiter plates. The usual alcohol precipitation steps were eliminated. This was done by simply adding 10μl of dilute dimethyl sulfate (1 mM), acetic acid (15 mM) or 0.1 mM potassium permanganate (for G+C, A+G, and T reactions, respectively) to 5 μl of DNA followed by 50μl of 1.3M piperidine. The reactions, lyophilization, resuspension, and loading were all done in the 96-well plates using multi-tipped pipets special designed for the 8×12 well format.

The pooled, reacted samples were then electrophoretically separated on sequencing gels by conventional means. Typically, the four sequencing reaction mixtures of twenty-four different pool samples were applied in separate lanes on each gel. The separated nucleotide patterns were then transferred to a nylon membrane, and fixed to the membrane (other solid media are equally suitable), as described by Church & Gilbert, supra.

Step 5.

Each nylon membrane, with each lane containing overlapping sequencing-fragments of 46 different 1 kb fragments, was then hybridized with one of the 92 probe oligonucleotides, each one of which is complementary of one of the tag sequences. Unreacted tag probe was then washed off with a 7-fold dilution of the hybridization buffer at 23° C., and the autoradiographic pattern of the treated gel recorded. Only those sequencing fragments containing the complementary tag sequence will hybridize with any given probe oligonucleotide, and thus be detectable by autoradiography. Hybridized probe was then removed, and the procedure repeated with another tag probe oligonucleotide. The nucleotide pattern fixed on the nylon membrane can be repeatedly hybridized in 7% SDS 770 mM sodium phosphate, pH 7.2 at 42° C., with a tag probe oligonucleotide, excess probe washed off, autoradiographed, then washed free of probe (by melting the 20 base pair DNA duplexes at 65° C. in low salt (2 mM tris-EDTA-SDS)), and reacted with another tag probe. Over 45 successive probings have been achieved. There is no reason to expect that this is the limitation on the number of successive probings possible on one membrane. Each tag probe oligonucleotide will detect only those sequencing fragments derived from whichever of the 46 original 1 kb fragments was cloned with the complementary tag probe oligonucleotide.

The hybridizations, washes and exposures were performed in an automated probing device (see below) with the membrane sealed in a container made of thin plastic (Scotchpak$^{TM}$ #229, about 60 μm thick). The solutions were introduced through a tube to the inside and the X-ray film pressed tightly against the plastic layer by applying pressure (e.g , 3 mm Hg air pressure above atmospheric pressure) to the film via a 4 kg flat weight on a constrained inflatable element, such as a plastic bag.

The membranes were marked with vector DNA used in a manner like ink on paper to automatically identify the membrane and the probe used by the hybridization properties of the DNA markings. Markings to identify the probe used consisted of one vector per dot or line corresponding to each probe, or any appropriate mixture of vectors or fragments thereof. Markings to identify the membrane were a mixture of all vectors, this will hybridize with all the probes used in sequencing procedures.

Internal standards were also provided in at least one lane in the gel. These known internal standards gave sequencing patterns which are useful for interpretation of unknown sequences. Specifically, during digital image processing of the film sequence data the prior knowledge of lane and band positions and shapes for the sequencing film can speed processing for all subsequent films prepared from the same membrane. Prior knowledge of reaction chemistry deviations and local gel artifacts seen in a standard sequencing reaction also helps in accurate estimation of errors for all subsequent films. For example, internal standards can be applied to each lane and discerned prior to probing with oligonucleotides. One such standard is the product of a sequencing reaction on a vector having no insert, thus providing a known DNA sequence. Such known DNA sequences provide ideal internal standards since the band shapes, lane shapes, and reaction chemistry visible from one probing are congruent with those in all subsequent probings. This aids the data reduction steps and the quantative recognition of trouble spots. This technique can also be used for mapping of restriction enzyme sites in DNA molecules.

Interpretation of the X-ray films generated by the above-process includes six steps to transform the raw data to an idealized form. The resulting data is interpreted to provide a DNA sequence and estimates of the liklihood of alternative interpretations made. The steps are: (a) to find the boundaries of the lanes and straighten them if necessary; (b) to adjust the interband distances; (c) to straighten the bands across each lane; (d) to adjust the interlane displacements; (e) to adjust the band thicknesses; and (f) to adjust the reaction specificities (i.e., to ensure that each band in each of the lanes in a set of reactions is a true band). Some of these steps are discussed by Elder et al. 14 Nuc. Acid. Res. 417, 1986.

Figure 5:
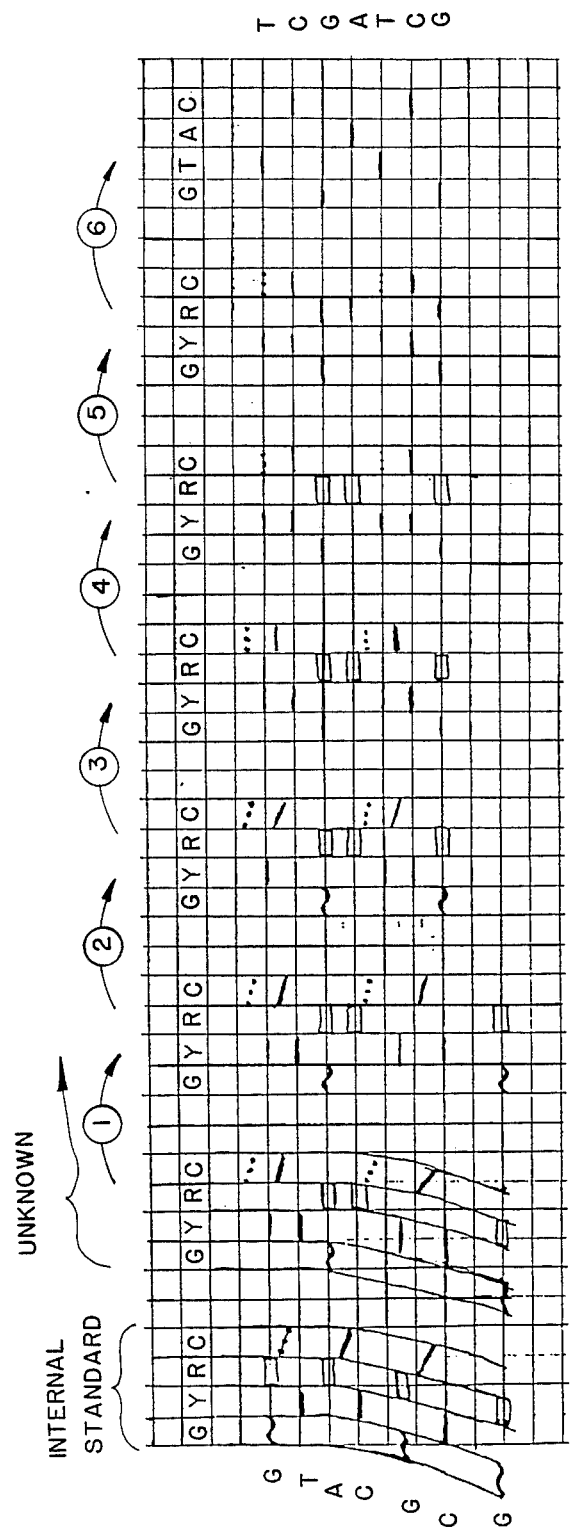
FIG. 5 is a diagrammatic representation showing data transformations from raw data to ideal data.

Referring to FIG. 5, a schematic example of band interpretation is provided. DNA sequencing reactions from an internal standard (left panel) and an unknown DNA sample (second panel from left) were placed in the same lanes of a gel and probed with appropriate probes. FIG. 5 is a schematic of the resulting X-ray films. As can be seen from the left two panels both the standard and the unknown deviate from an ideal result (shown in the right panel) in an identical manner. The DNA sequence of the standard is provided on the left of FIG. 5. Using this sequence it is possible to determine which bands on the film represent true bands, rather than artifacts. From this analysis the DNA sequence of the unknown can then also be determined by making allowance for artifacts detected in the standard sample. Thus, referring to FIG. 5, the transformation steps described above can be applied. In the first step lane curvature is straightened in all four lanes; in the second step interband distances are made equal; in the third step band curvature is straightened; in the fourth step severe interlane displacement in the C lane relative to the other three lanes is adjusted; in the fifth step thick bands in the R lane are made thinner; and in the sixth step false bands are removed. After these steps the ideal result is determined and thence the DNA sequence of the unknown (shown on the right of FIG. 5).

Each adjustment that involves manual or automatic pattern recognition on the entire film data set can take about an hour. By using the above multiplexing sequencing method with an internal standard of known sequence each of the adjustments can be more accurately determined than for an unknown sequence, and then applied to each set of unknown film data obtained from subsequent probings of the same membrane. Thus, one standard pattern can be used for a large number of later probings of the same membrane. The transformation requirements can be memorized by the computer and recalled as necessary.

Automated Probing Device

An automated probing device is useful for automation of the visualization of latent multiplexed DNA sequences immobilized on nylon membranes, or for any other process where multiple cycles of probing are necessary.

In general, after the DNA to be probed has been transferred and crosslinked to a membrane support, eg., a nylon membrane, the nylon membrane is heat-sealed into a polyester/polyethylene laminate bag such as Scotchpak$^{TM}$, the automated probing device performs the following steps: (a) 100 ml of prehybridization buffer (7% SDS, 10% PEG (MW 6000), 0.13M sodium phosphate pH 7.2, and 0.25 M NaCl) is introduced into the bags and the membranes equilibrated; (b) this buffer is removed and 90 ml of hybridization buffer with probe (5 pM radiolabeled oligonucleotide in prehybridization buffer) is introduced; followed by a 10 ml chase of prehybridization buffer; (c) the membranes are then incubated 4 to 16 hours at 42° C.; (d) wash buffer (1% SDS, 70 mM sodium phosphate pH 7.2) is introduced, incubated at room temperature for 45 minutes and removed; the wash is repeated a minimum of 5 times; (e) after the last wash, X-ray films are placed over the membranes and exposed. To ensure good contact between the film and membrane an air bag is inflated directly over the film; (f) after exposure the air bag is deflated by use of a vacuum and the films processed; (g) the probe is removed with hot stripping buffer (2 mM EDTA,TRIS base pH 7.5, 0.2% SDS at 80° C.) and the cycle repeated with a new probe.

Figure 6:
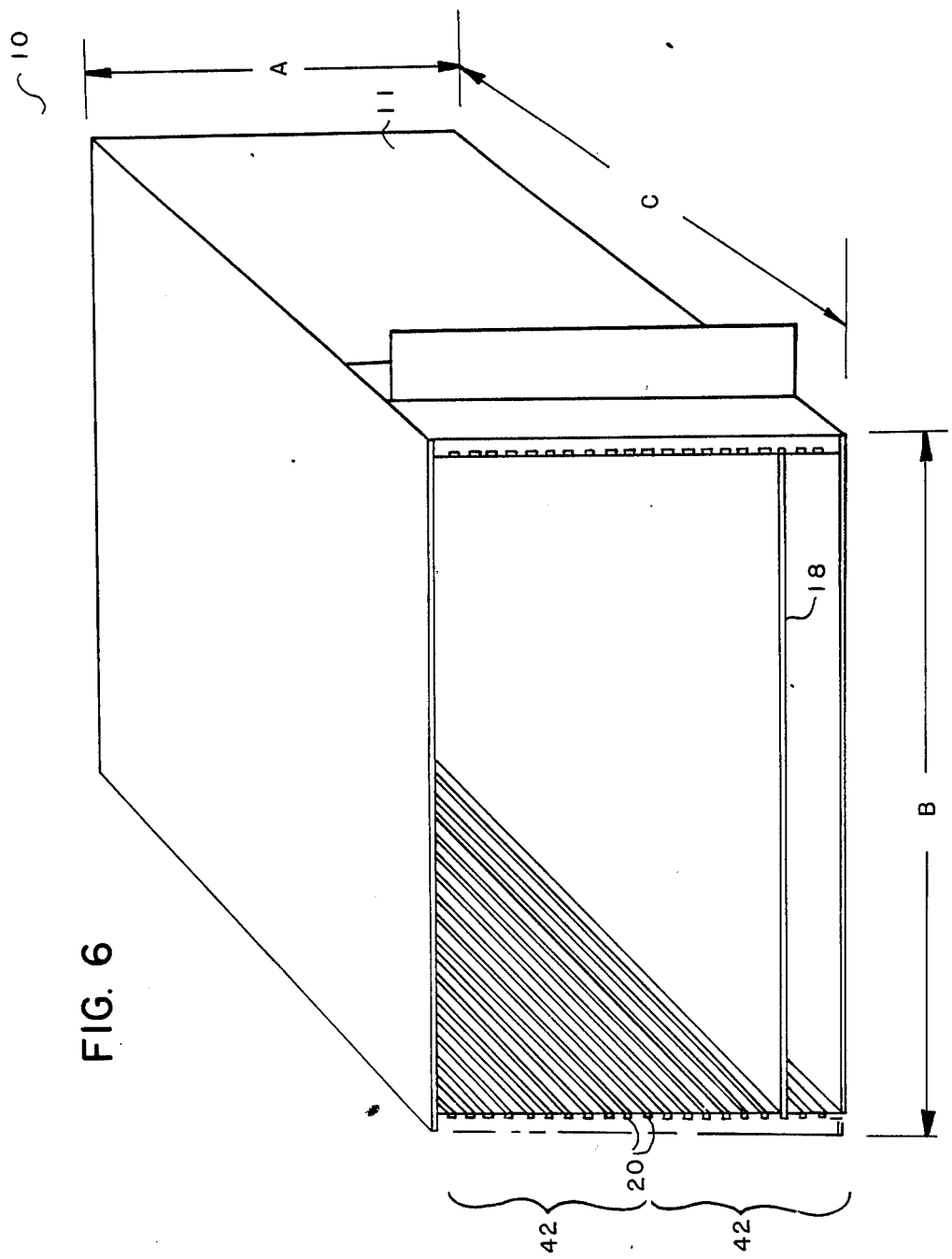
FIG. 6 is an isometric view of a container for automated probing of membranes.
Figure 7:
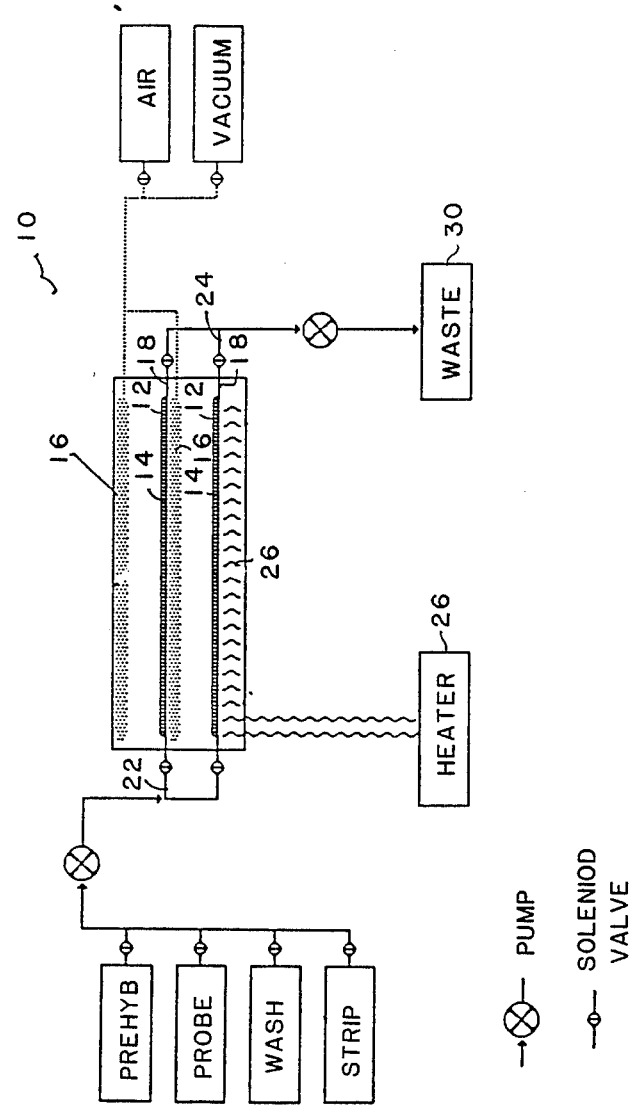
FIG. 7 is a diagrammatic representation of components of an automated probing device.

Referring to FIGS. 6 and 7, automated prober 10 is formed of a light-tight aluminum housing 11, having a series of grooves 20 for slideably accepting a series of shelves 18. Shelves 18 are spaced apart about 0.4" to allow a re-usable pouch 12 formed from plastic of thickness 0.65 micron, an X-ray film (not shown) and an air bag 16 to be sandwiched between each shelf 18. Housing 11 has a height A of 10.75", a width B of 20" and a depth C of 24". Each pouch 12 is provided with an inlet pipe 22 and an outlet pipe 24, and the housing is heated by heater 26. A door (not shown) of thickness 0.25" is provided with a 0.125" neoprene light-tight gasket seal and a latch. Automated prober 10 is assembled and manufactured by standard procedure. Light-tight construction of automated prober 10 allows exposures to be performed outside of a photographic darkroom; and aluminum housing 11 provides efficient attenuation of beta particles from $^{32}P$ decay, with minimal secondary X-ray formation.

Re-usable pouches 12 allow tight contact with the X-ray film to be exposed, without need for pouch disassembly. Membranes 14 are fixed (by heat tacking of corners) inside each pouch 12 to prevent movement and creasing of membranes 14. In addition to membranes for multiplex sequencing the automated probing device is capable of accommodating membranes from standard restriction digest transfers, and dot and slot blots used in diagnostics. The horizontal format allows uniform spatial distribution of a probe, without need for mesh supports. The rigid bookshelf type structure allows air bags 16 to expand between shelves 18 to ensure tight contact between each X-ray film and an adjacent membrane 14. Each shelf 18 easily slides out of grooves 20 for membrane replacement.

A computer (not shown) controls temperature, liquid, air, and vacuum flow. Only the X-ray films and vessels containing liquid input and output have to be manually changed.

Also provided is a heated, ventilated output waste vessel 30 which allows 100-fold concentration of liquid wastes, thereby reducing disposal costs.

Automated prober 10 is constructed as repeating shelf units 42 of ten membranes, each repeat of ten membranes having dedicated reservoirs and valves for service buffers including hybridization buffer, probe, wash solution and stripping buffer. Each individual membrane has its own input valve. The waste output valves are placed in series with a 12VDC-controlled Gorman-Rupp reciprocating pump; the buffer input valves are also placed in series via a 12VDC-controlled Gorman-Rupp reciprocating pump. Air input is used to inflate air bags for X-ray film exposures. These air bags may be covered by conductive foam to enhance membrane contact. A house vacuum is used to evacuate the airbags after exposure. During probing the temperature is maintained at 42° C. by heating mats 26 placed inside the top and bottom of the apparatus.

Computer control is by TRS-80 Model 102 which controls the valves via a CIP/35 serial controller (SIAS Engineering). A BASIC program controls all buffer inputs and output by timing loops; thus it is important to calibrate the flow rates before setting parameters. Parameters are set by creating a text file that can be opened and read by the BASIC program The input file has lines that have a number as the first element followed by tab before any descriptors are used. The line order is:

1. - membrane number (1-10)
2. - repeat units (1-13)
3. - minimum membrane number
4. - maximum membrane number
5. - prehyb input time (min)
6. - —prehyb incubate time (min)
7. - prehyb output time (min)
8. - probe input time (min)
9. - probe chase time (min)
10. - probe incubation time (hours)
11. - probe output time (min)
12. - wash input time (min)
13. - wash incubation time (min)
14. - wash output time (min)
15. - number of washes (integer)
16. - strip input time (min)
17. - strip incubate time (min)
18. - strip output time (min)

Other embodiments are within the following claims.

We claim:

1. A method for sequencing a DNA specimen comprising:
   (a) providing a set of at least two vectors, each vector of said set comprising a cloning site and including at least one tag sequence at a position within 50 bases of said cloning site, each tag sequence in each vector differing from each tag sequence of every other vector of said set, and each being incapable of hybridizing to said DNA specimen under stringent conditions,
   (b) providing a first and a second DNA sequence from said DNA specimen, said first DNA sequence being different from said second DNA sequence,
   (c) ligating said first DNA sequence into the cloning site of one of said vectors, and said second DNA sequence into the cloning side of a second of said vectors, thereby producing a plurality of hybrid vectors,
   (d) providing a pool of said hybrid vectors,
   (e) treating separate aliquots of said pool in a plurality of vessels to produce fragments comprising said tag sequence, wherein said fragments in each vessel differ in length from each other and all terminate at a fixed known base or bases, wherein said fixed known base or bases in one of said vessels differ from said fixed known base or bases in another of said vessels,
   (f) separating said fragments comprising tag sequences from each said vessel according to their size,
   (g) hybridizing the separated fragments of step (e) under stringent conditions with a first oligonucleotide probe able to hybridize specifically with one of said tag sequences, and
   (h) detecting the pattern of hybridization wherein said pattern reflects the nucleotide sequence of said DNA specimen.

2. The method of claim 1 wherein the pattern detected in step (h) reflects the nucleotide sequence of said first DNA sequence and said method further comprises the steps of rehybridizing the separate fragments of step (f) under stringent conditions with a second oligonucleotide probe different from the first and detecting a second pattern of rehybridization wherein said second pattern of hybridization reflects the nucleotide sequence of said second DNA sequence.

3. The method of claim 1 or 2 in which each said vector comprises two said tag sequences.

4. The method of claim 3 in which said two tag sequences on the same vector are different from each other.

5. The method of claim 1 or 2 further comprising binding the fragments of step (e) to a solid support prior to said hybridizing.

6. The method of claim 1 or 2 wherein said stringent hybridization conditions comprise conditions in which mismatched duplexes are melted to form single stranded molecules.

7. A method for simultaneously sequencing multiple DNA molecules comprising,
   (a) providing a pool of individually different DNA tag sequences, each tag sequence in said pool being foreign to, and incapable of hybridizing under stringent conditions to, any of said DNA molecules to be sequenced;
   (b) from separate aliquots of said pool of tag sequences, generating a plurality of sets of hybrid DNA fragments in separate vessels, said hybrid fragments in each vessel differing in length from one another and terminating in a fixed known base or bases, wherein said fixed known base or bases in one of said vessels differ from said fixed known base or bases in another of said vessels;
      (i) each of said fragments comprising at least one of said tag sequences and at least part of one and only one of said DNA molecules to be sequenced, each of said fragments that includes part of any given one said DNA molecules to be sequenced having a tag sequence that is different from each of the tag sequences in fragments that include part of any other one of said DNA molecules to be sequenced,
      (ii) each fragment of a first set of said hybrid DNA fragments comprising a first one of said tags, said first set of fragments comprising fragments of different lengths of a first one of said DNA molecules to be sequenced; and each fragment of a second set of said sets fragments comprising a second one of said tags, said second set of fragments comprising fragments of different lengths of a second one of said DNA molecules to be sequenced,
   (c) separating said first and said second set of fragments according to their size, yielding size-separated fragments,
   (d) hybridizing said sizeseparated fragments under stringent conditions with a first oligonucleotide probe able to hybridize specifically with said first one of said tag sequences,
   (e) detecting a first pattern of hybridization with said first probe, wherein said first pattern reflects the nucleotide sequence of at least a part of said first DNA molecule to be sequenced,
   (f) hybridizing said size separated fragments under stringent conditions with a second oligonucleotide probe able to hybridize specifically with said second one of said tag sequences, and
   (g) detecting a second pattern of hybridization with said second probe, wherein said second pattern reflects the nucleotide sequence of said second DNA molecule to be sequenced.

8. The method of claim 7 in which each said hybrid DNA fragment comprises two said tag sequences.

9. The method of claim 8 in which said two tag sequences are different from each other.

10. The method of claim 8 or 9 further comprising binding the fragments of step (e) to a solid support prior to said hybridizing.

11. The method of claim 8 or 9 wherein said stringent hybridization condition comprises conditions in which mismatched duplexes are melted to from single stranded molecules.

12. The method of claim 7 in which said pool of DNA tag sequences is provided by providing a set of at least two vectors, each vector of said set comprising a cloning site and including at least one of said tag sequences at a position within 50 bases of said cloning site, each tag sequence in each vector differing from each tag sequence of every other vector of said set, ligating said first one of said DNA molecules to be sequenced into the cloning site of one of said vectors, and ligating said second one of said DNA molecules to be sequenced into the cloning site of a second of said vectors, and then providing a pool of the resulting hybrid vectors comprising said tag sequences.

* * * * *